US010874863B2

(12) United States Patent
Rump et al.

(10) Patent No.: US 10,874,863 B2
(45) Date of Patent: Dec. 29, 2020

(54) ELECTRODE LEAD, IMPLANT, AND METHOD FOR IDENTIFYING AN ELECTRODE LEAD

(71) Applicant: BIOTRONIK SE & Co. KG, Berlin (DE)

(72) Inventors: Jens Rump, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 341 days.

(21) Appl. No.: 15/667,684

(22) Filed: Aug. 3, 2017

(65) Prior Publication Data

US 2018/0050189 A1 Feb. 22, 2018

(30) Foreign Application Priority Data

Aug. 16, 2016 (EP) .................... 16184297
Aug. 16, 2016 (EP) .................... 16184298
Aug. 16, 2016 (EP) .................... 16184299

(51) Int. Cl.
| | | |
|---|---|---|
| *A61N 1/372* | (2006.01) | |
| *A61N 1/05* | (2006.01) | |
| *A61N 1/04* | (2006.01) | |
| *A61N 1/08* | (2006.01) | |
| *A61N 1/375* | (2006.01) | |
| *A61B 90/98* | (2016.01) | |
| *A61N 1/02* | (2006.01) | |

(Continued)

(52) U.S. Cl.
CPC .......... *A61N 1/37229* (2013.01); *A61B 90/98* (2016.02); *A61N 1/025* (2013.01); *A61N 1/0488* (2013.01); *A61N 1/05* (2013.01); *A61N 1/08* (2013.01); *A61N 1/37* (2013.01); *A61N 1/3752* (2013.01); *A61N 1/04* (2013.01); *G01R 19/2503* (2013.01)

(58) Field of Classification Search
CPC .. A61N 1/37229; A61N 1/025; A61N 1/0488; A61N 1/3752; A61N 1/37223; A61N 1/05; A61N 1/08; A61N 1/37; A61N 1/04; A61B 90/98; G01R 19/2503
See application file for complete search history.

(56) References Cited

U.S. PATENT DOCUMENTS 5,720,293 A 2/1998 Quinn et al.
5,755,742 A 5/1998 Schuelke et al.
(Continued)

*Primary Examiner* — Tammie K Marlen
(74) *Attorney, Agent, or Firm* — Buchanan Ingersoll & Rooney PC

(57) ABSTRACT

An implant including a hermetically tightly sealed housing, wherein a control unit is arranged in the housing, and including a header, which is secured to the housing and includes at least one socket for connection to a plug of an electrode lead, and includes a communication antenna, which is electrically connected to the control unit. To achieve a reliable identification of the electrode lead with a low energy expenditure, the header has, in the region of the at least one socket, at least one electromagnetic transmission element electrically connected to a contact element which is provided on the inner wall of the at least one socket or to the ground of the implant and to the control unit, wherein the electromagnetic transmission element is electromagnetically or inductively coupled to the communication antenna. A corresponding electrode lead and a corresponding method for identifying an electrode lead are also contemplated.

6 Claims, 10 Drawing Sheets

(51) Int. Cl.
*A61N 1/37* (2006.01)
*G01R 19/25* (2006.01)

(56) References Cited

U.S. PATENT DOCUMENTS

| | | |
|---|---|---|
| 7,713,194 B2 | 5/2010 | Zdeblick |
| 7,983,763 B2 | 7/2011 | Stevenson et al. |
| 2003/0018369 A1 | 1/2003 | Thompson et al. |
| 2004/0073265 A1 | 4/2004 | Scheiner |
| 2006/0212083 A1 | 9/2006 | Scheiner |
| 2006/0212096 A1 | 9/2006 | Stevenson |
| 2007/0203547 A1 | 8/2007 | Costello et al. |
| 2008/0065181 A1 | 3/2008 | Stevenson |
| 2011/0112609 A1 | 5/2011 | Peterson |
| 2012/0123496 A1 | 5/2012 | Schotzko et al. |
| 2014/0330347 A1 | 11/2014 | Simms, Jr. |
| 2014/0343633 A1 | 11/2014 | Kaula et al. |

ELECTRODE LEAD, IMPLANT, AND METHOD FOR IDENTIFYING AN ELECTRODE LEAD

CROSS-REFERENCE TO RELATED APPLICATIONS

This patent application claims the benefit of and priority to co-pending European Patent Application No. EP 16184299.2, filed on Aug. 16, 2016, European Patent Application No. EP 16184297.6, filed on Aug. 16, 2016, and European Patent Application No. EP 16184298.4, filed on Aug. 16, 2016, which are all hereby incorporated by reference in their entireties.

BACKGROUND OF THE INVENTION

Technical Field

The present invention relates to an implant with a hermetically tightly sealed housing, wherein a control unit is arranged in the housing, and with a header secured to the housing and comprising at least one socket for connection to a plug of an electrode lead and comprising a communication antenna, which is electrically connected to the control unit, a method for identifying an electrode lead, and an electrode lead.

Description of the Related Art

Implants (implantable medical devices, or IMDs) such as cardiac pacemakers, defibrillators or neurological devices such as brain pacemakers for deep brain stimulation, spinal cord stimulation devices, transcutaneous electrical nerve stimulators (TENS), devices for muscular stimulation therapy, or diagnosis devices, which examine the chemical properties of a patient's blood or other body parts, or other bodily properties and parameters, often use electrode leads, which are guided into the patient's body and remain there at least for the duration of the treatment or measurement. The electrode leads are electrically conductively connected to the implant.

The implants usually comprise a biocompatible housing with an associated electrical/electronic circuit and a power supply, for example, a battery. The electrical/electronic circuit, a control unit electrically connected to the circuit, and a power supply are often arranged within the housing, which is hermetically tightly sealed. The implant has at least one socket, to which one or more electrode leads can be connected, for example, by means of a plug. An electrode lead serves to transfer electrical energy (an electrical potential) and/or data from the housing to the treated or examined body part, and vice versa. For this purpose, an electrical connection must be established between the electrical/electronic components arranged in the housing interior, including the control unit and the electrode lead or the electrode leads. This electrical connection is generally established by means of what is known as a header. A feedthrough connected to the housing ensures at least one electrical connection between the interior of the housing and the exterior and is also responsible for the hermetic sealing of the housing. The header secured at the housing, covering the feedthrough leads the electrical connection of the feedthrough further to the at least one socket, which serves for electrical and mechanical connection to an electrode lead. The header and feedthrough can also be used as a combined module. Hereinafter, any module of the implant which establishes the electrical connection of the elements arranged inside the hermetically tightly sealed housing to the outside and which has at least one socket for plugging in the at least one plug is referred to as a header.

Within the scope of the present invention, the term "electrode lead" is understood to mean a lead comprising an electrical conductor or a plurality of electrical conductors, together with the encasing insulation sheath electrically insulating the one or more electrical conductors externally and with respect to one another as appropriate, and all further functional elements fixedly connected to the lead. The electrode lead generally comprises, at its distal end, electrodes which are arranged, for example, as rings along the electrode lead or in a form of a matrix on a patch. Some electrode leads also comprise, at their distal end, what is known as an electrode tip, by means of which the electrical energy from the conductor or conductors is introduced into the tissue to be treated. An electrode tip is often provided with anchor elements or retaining structures, by means of which it can be ensured that the spatial position of the point of transition of the electrical energy into the tissue to be treated remains constant. The electrode tip can be formed as a sensing electrode, stimulation electrode, or measurement electrode. Additionally or alternatively to an electrode or an electrode tip, electrode leads can also comprise one or more sensors for detecting parameters. The electrode lead generally also has, for example, at its proximal end, a plug, by means of which the electrode lead can be connected to an implant, wherein the plug for this purpose is plugged into a corresponding socket of the implant. The plug has one or more contact elements (e.g., poles, connection points), wherein each contact element is connected to exactly one electrical conductor of the electrode lead. Accordingly, a contact element of the socket is provided in the socket for each contact element of the electrode lead.

A plurality of electrode leads are often connected to modern implants, for example, a multi-chamber cardiac pacemaker, an implantable cardioverter-defibrillator (ICD) or a neurostimulator. Here, it is sought to design the electrode leads and connection points thereof to be as thin and/or small as possible. However, this makes it difficult to mark the plugs and connection points in a clearly visible manner and also makes it difficult to distinguish between the electrode leads. In addition, with an increasing number of electrode leads, there is an increased risk that individual electrode leads will be confused and/or incorrectly connected. It is therefore desirable if an implant can detect which electrode leads are connected, so that it can control these suitably. In addition, for operation of the implant, it is helpful if the electrode leads and/or properties thereof are identifiable for the implant.

U.S. Publication No. 2004/0073265 describes a device which offers a possibility for detecting incorrectly connected coronary leads and/or incorrect connections to heart rhythm management devices. For this purpose, a voltage introduction device of a pacemaker generates a voltage pulse between an electrode which is connected by means of a lead to the pacemaker and a header or housing electrode of the pacemaker. The housing electrode sends a connection signal. The electrode is used to measure a corresponding connection signal with use of the lead. A measurement module of the device also measures one or more properties of the corresponding connection signal, such as its current intensity, voltage, impedance and/or its time delay (after transmission of the voltage pulse). The signal properties can be influenced by one or more leads and/or by the communicating tissue and liquids (for example, a heart inclusive of one or more chambers thereof) arranged in-between. A comparison module of the pacemaker can determine, on this basis, whether the lead has been correctly guided to a contact of the pacemaker, wherein one or more properties of the corresponding connection signal are compared with suitable preselected value ranges. By way of example, a measured impedance can be compared with an expected impedance range. The device described in the above-mentioned document therefore does not identify the lead selectively, but instead tests whether the corresponding comparison signal received via a lead following excitation of the body by a voltage pulse of a housing electrode of the pacemaker has properties within a predefined value range. The properties of the corresponding comparison signal are also determined by the excited bodily tissue between the housing electrode of the pacemaker and the receiving electrode. Only very large deviations, as occur due to an unconnected or completely incorrect type of lead, can be reliably attributed to the lead, whereas smaller deviations can be caused by the body. The above-mentioned device therefore cannot ensure a reliable and selective detection and distinction of electrode leads having similar properties.

A similar device is also disclosed in U.S. Publication No. 2006/0212083. In this document, as well it is stressed that the signal properties are influenced by the leads and/or by the communicating tissue and liquid arranged in-between.

U.S. Publication No. 2011/0112609 describes a system for spinal cord stimulation comprising at least one implantable stimulation lead. It comprises, in particular, a medical programming unit and an implantable pulse generator, which is connected to one or more implantable stimulation leads, which each carry a multiplicity of electrodes. The stimulation lead has one or two lead bodies. The electrodes fit perfectly in the epidural space of the spinal cord. Since the tissue there is conductive, electrical measurements can be taken between the electrodes. A control circuit of the implantable pulse generator detects electrical measurements of this type, such that the medical programming unit can automatically identify the individual lead bodies connected to the implantable pulse generator. The electrical measurements of the control circuit for identification of the connected lead bodies are field potentials. The control circuit can also measure the impedance at each electrode in order to determine the coupling efficiency between each of the electrodes and the tissue and in order to determine the fault detection with regard to the connection between the electrode and the analogue output circuit of the implantable pulse generator. In the known system, it is disadvantageous that the identification is not performed by the implantable pulse generator itself, but instead by an additional medical programming unit.

U.S. Publication No. 2012/0123496 relates to the detection of the connection and the identification of the type of an implanted lead for an implanted medical device. The device has a processor, which can determine the connection and also the lead type. A signal measurement module firstly checks the connection of the leads by checking values of electrical parameters during a signal between at least two electrodes, in particular, the impedance. One or more leads can have active electronics integrated therein, which electronics comprise one or more modular circuits integrated therein depending on whether the lead is unipolar or multipolar. Each of the modular circuits is able to control a multiplicity of electrodes of the lead and includes a circuit arrangement electrically connected to one or more electrodes of the lead. As such, each of the modular circuits of a lead acts as an interface between the implanted medical device and the electrodes to which the modular circuit is connected. In order to measure the impedance, the processor of the device controls the modular circuit so that this delivers a voltage pulse between a first and a second electrode. The signal measurement module measures the resultant current and the processor derives from this the impedance value. In a further step, the processor sends a query signal along a first conductor of the lead in order to obtain a response from the modular circuits via a second lead. Such a response from each modular circuit provides the processor with information relating to the modular circuit and the electrodes controlled thereby. In a further configuration step, the processor sends a signal via the first lead. The configuration step includes the fact that the active configuration of the modular circuits is programmed. Reference is made to document U.S. Pat. No. 7,713,194 with regard to lead designs and active electronics or modular circuits used therein. In accordance with this document, the modular circuit is designed in such a way that it is controlled by a bus. U.S. Publication No. 2012/0123496 therefore describes the fact that the additional interface electronics of the modular circuits can detect an electrode lead, which therefore can be determined. A disadvantage of the known device is that complex modular circuits with active electronics for control of the electrodes have to be implemented and programmed. Furthermore, the information relates only to the modular circuits and the electrodes connected thereto, not to the lead as a whole.

A method and a device for the automatic detection of implantable medical leads and configuration thereof are presented in U.S. Publication No. 2003/0018369. For this purpose, a first communication circuit, which stores data such as model and serial numbers, technical information and calibration data, is connected to the lead or integrated therein. This first communication circuit comprises a receiver and a transmitter to receive data signals from an external source. It can thus be programmed with identification data, calibration data and other data at the time of manufacture. The first communication circuit is embodied as a passive transponder and, besides the receiver and transmitter, also comprises an energy coupler for power supply and a control circuit connected to a non-volatile memory. The control circuit delivers the lead information stored in the memory to the transmitter/receiver of the transponder, which transmits the data via RF or other communication. During the implantation of the lead or thereafter, the information can be transferred to a second communication circuit outside the lead. The transferred data can be used for identification of the lead, recorded in a patient record, and transferred to a central memory for use by health service providers. The lead can be automatically detected on the basis of the transponder, and the data stored in the memory can be directly transferred and forwarded. Besides a transmitter and receiver, however, the transponder also requires a separate power supply, a control unit, and a programmable, digital memory. The overall construction of the lead is therefore relatively complex and costly.

U.S. Publication No. 2014/0343633 also presents an electrically identifiable electrode lead comprising an identification module which has at least one filter, a power converter, a communication circuit, a load switch, and a memory unit, such as an EPROM, for storing an identification code. Before the implant is introduced, each lead is implanted and connected to the implantable pulse generator (or an external pulse generator), which then reads out self-identifying data from the identification module and can transmit this information to an external device, such as the clinician programmer device. For this purpose, the identification module can store up to 32 bytes of data. This method is repeated for each lead that is implanted. The identification module uses two provided contacts of the lead for connection to the implantable pulse generator. As in the document mentioned beforehand, a digital memory is required for this known electrode lead as well, and the construction of the identification module is similarly complex.

U.S. Publication No. 2006/0212096, U.S. Publication No. 2008/0065181 and U.S. Pat. No. 7,983,763 disclose devices for identifying an implantable medical device and an implanted conductor system, in which an RFID tag with an RFID chip is arranged in the insulation surrounding the conductor or is arranged in the header of an implantable device. A reader is also provided, which can wirelessly read the data stored in the RFID chip relating to the unit, the conductor system, the manufacturer or the patient. However, the information that can be read does not contain any details regarding the current arrangement and/or the connection of the electrodes. In addition, it is disadvantageous in the case of the solutions explained in these documents that a relatively large amount of energy has to be consumed in order to query the data from the implant and in order to activate the chip. Additional units are used for this purpose, however, these place the patient under a significant SAR load (SAR=specific absorption rate–measure of the rate at which an electromagnetic field is absorbed by human tissue).

One object of the present invention therefore lies in creating an electrode lead or a corresponding implant so that the electrode lead can be identified reliably and clearly, including in respect of its properties and the socket connected to the electrode lead or the channel connected to the electrode lead. The implant and the electrode lead, however, at the same time should be of simple construction, should operate in an energy-saving manner, and should be able to be manufactured economically. The electrode lead should be modified to the least possible extent. A further object lies in specifying a simple method for identifying an electrode lead, which method enables an unambiguous assignment of electrode conductor information to a socket of the implant or to the corresponding channel of the implant (for example, atrium, ventricle, coronary sinus, region of the spinal cord or brain, stomach, bladder, vagus nerve, phrenic nerve or skeletal muscle).

The present invention is directed toward overcoming one or more of the above-mentioned problems.

BRIEF SUMMARY OF THE INVENTION

At least the above object(s) is achieved by an implant having the features of claim 1.

At least the above object(s) is achieved in particular by an implant in which the header, in the region of the at least one socket, has at least one electromagnetic transmission element, which is electrically connected to a contact element which is provided on the inner wall of the at least one socket, wherein the electromagnetic transmission element is coupled electromagnetically or inductively to the communication antenna.

The electromagnetic or inductive coupling between the electromagnetic transmission element and the communication antenna is promoted in that the smallest distance between the communication antenna and the electromagnetic transmission element is preferably less than 12 mm. It is also advantageous if the communication antenna and the electromagnetic transmission element run in parallel over a conductor portion of at least 5 mm. The electromagnetic transmission element is preferably formed as an antenna or electrical conductor component (e.g., electrical conductor, conductor loop). The electromagnetic transmission element and/or the communication antenna are/is arranged in or on the header, preferably embedded in the header.

In order to attain the best-possible coupling between the communication antenna and the electromagnetic transmission element, the system is dimensioned in one exemplary embodiment such that, at the point of the transmission frequency, the power transmitted between the communication antenna and the electromagnetic transmission element is at most 10 dB below the maximum that would occur at resonance of the system consisting of communication antenna and electromagnetic transmission element. The magnetic flux, in a preferred exemplary embodiment, should flow through the communication antenna and the electromagnetic transmission element optimally so that the magnetic coupling factor is preferably at least 0.1. The communication antenna, by way of example, can also be used for the communication between implant and a further unit, such as an external communication unit for contacting a data and service center.

The above-described implant according to the present invention is used for the identification of the electrode lead, such that no additional unit is necessary for this purpose. The implant according to the present invention additionally manages with a small number of additional parts. Furthermore, as a result of the solution according to the present invention, there is no risk posed to the therapeutic path due to serial galvanic coupling or additional electrical components. The solution according to the present invention is additionally characterized by a low power requirement. In addition, no provisions are necessary in order to bypass the function of EMI protection filters (EMI=electromagnetic interference) in order to read the information from the electrode lead.

In one exemplary embodiment, the electromagnetic transmission element is connected to the housing of the implant, which is electrically conductive, via a capacitor. High frequencies are hereby discharged directly to the housing of the implant. As a result, no communication signals can enter the housing. Here, in a first alternative, the capacitor can be dimensioned such that it is short-circuited at the transmission frequency at which the transmission element communicates with the communication antenna (i.e., its impedance is less than 1.5Ω). In this alternative, the capacitance of the capacitor is greater than 500 pF, for example. In an alternative embodiment, the capacitor is designed such that the best-possible coupling between communication antenna and electromagnetic transmission element is reached at the transmission frequency, i.e., the transmission frequency is close to the resonance frequency of the circuit of the communication antenna. In this case, the capacitance of the capacitor is preferably less than 1.5 nF.

In order to enable a communication of the communication antenna with an external unit (for example, for the contacting of a data and service center or radio telemetry) and an identification of a connected electrode lead, wherein both operating modes can preferably also occur simultaneously, the circuit of the communication antenna preferably has at least two resonances. At least two separate channels for the communication antenna are provided as a result.

The implant preferably has multiple sockets in the header, and the number of the electromagnetic transmission elements corresponds with the number of sockets, i.e., the number of sockets is equal to the number of electromagnetic transmission elements. Here, merely a sole communication antenna is provided in and/or on the header and is electromagnetically or inductively coupled to all transmission elements arranged in and/or on the header.

As described below in detail, the control unit generates a query signal for identification of the at least one connected electrode lead and transmits this query signal to the communication antenna. In a further exemplary embodiment, the control unit is designed in such a way that it generates a separate query signal for each socket of the multiplicity of sockets following the occurrence of a predetermined event. A predetermined event of this type is, for example, the connection of the electrode lead, i.e., the correct plugging of the plug into a socket of the implant or the establishment of a galvanic connection between corresponding contact elements of the plug and the socket in which the plug is plugged.

In a further exemplary embodiment, the implant can comprise a detection unit which detects the connection of the electrode lead to the implant. The detection unit therefore serves to identify an above-described predetermined event. The detection unit is preferably connected to the control unit of the implant. By way of example, the detection unit can transmit a trigger signal to the control unit if the detection unit identifies that a plug of an electrode lead has been correctly plugged into a socket of the implant, such that the galvanic contact is established.

At least the above object(s) is also achieved by an electrode lead comprising a plug for connection to an implant, comprising at least one electrical conductor and an insulation sheath insulating the at least one electrical conductor, wherein the electrode lead additionally comprises a hermetically sealed RFID chip embedded:
  in the insulation sheath, and/or
  in the plug, or
  in an insulating body of a separate add-on part connectable, preferably in a positively engaged manner, to the insulation sheath or the plug,
wherein the RFID chip is electrically connected to a conductor loop or to at least one contact element arranged on the plug. By way of example, the RFID chip is suitable for UHF technology, i.e., frequencies greater than 800 MHz. There is no RFID antenna provided in the circuit of the RFID chip. In accordance with the present invention, the RFID chip, instead, when plugged into a socket of the implant is connected galvanically or via an electromagnetic field and the electrical conductor or a contact element of the electrode lead to the electromagnetic transmission element arranged in the header of the implant. The space on the electrode lead required by the additional component (RFID chip) is hereby minimized. The mechanical loading of the RFID chip is therefore very low. The add-on component with the RFID chip can measure, for example, a length of 500 µm and a thickness of 100 µm. The RFID chip is preferably galvanically connected to the contact element having the greatest inductance and/or resistance value compared with other contact elements of the electrode lead. The losses of the signals exchanged with the RFID chip are thus minimized.

The RFID chip of the electrode lead according to the present invention preferably comprises a memory unit for storing information to be transmitted to the implant. Alternatively, the information to be transmitted can also be generated by the circuit of the RFID chip in the event of activation of the RFID chip.

As already explained above, the RFID chip, in one exemplary embodiment, is galvanically connected to a contact element or the electrical conductor of the electrode lead. The electrical conductor of the electrode lead also has a galvanic connection to a contact element. The contact element is therefore preferably formed as a therapeutic contact element or as a separate contact element different from a therapeutic contact element. Each contact element, i.e., the contact element of the RFID chip or the contact element of the electrical conductor, is formed, for example, as a metallized area, preferably made of gold or platinum, arranged externally on the surface of the plug of the implant. Each contact element forms a galvanic connection to a corresponding contact element or pole, which is arranged on the inner wall of the socket of the implant, when the plug of the electrode lead is correctly plugged into the socket of the implant. The contact element directly connected to the RFID chip, by way of example, can be formed as a metallized contact ring, similarly to a contact sleeve for the contacting of ring electrode and tip electrode, or as a metallized sealing lip or plurality of metallized sealing lips.

In a further embodiment, the RFID chip can additionally be galvanically connected to a larger metallic element (for example, a metal ring), which is capacitively coupled to an electrical conductor of the electrode lead and thus serves as a ground plane of the RFID chip. The larger metallic element has an area of at least 10 $mm^2$, if the larger metallic element is of a planar design (for example, a metal ring). If, for example, meandering metallic elements are used, a smaller surface can be sufficient. This capacitive coupling preferably occurs in this case at an electrical lead other than that to which the RFID chip is galvanically connected. This second electrical lead is preferably connected to the ground of the implant if the electrode lead is plugged into the implant. When plugging the plug of the electrode lead into the socket of the implant, a connection of the RFID chip to the ground of the implant is thus achieved via the metallic element and the capacitive coupling.

If, in an alternative embodiment, the RFID chip is connected to a conductor loop, this is designed in such a way that there is an electromagnetic coupling to an electrical conductor of the electrode lead.

As a result of the correct plugging of the plug of the electrode lead into the socket of the implant, a spatially close arrangement between RFID chip, communication antenna and transmission element is provided in accordance with the invention, so that a good coupling is achieved between the aforesaid elements, even in the event of poor contacting.

In a preferred embodiment, the RFID chip is connected on one side to a first contact element and on the other side to a second contact element of the electrode lead. The implant accordingly has a first electromagnetic transmission element, which is electrically connected to the first contact element (e.g., pole, connection point) of the socket, and a second electromagnetic transmission element, which is electrically connected to the second contact element of the socket. Both electromagnetic transmission elements can be used for the identification of an electrode lead.

It is advantageous if the RFID chip is active or passive. An active RFID chip is understood to mean an RFID chip which, after receiving a signal via the electromagnetic transmission element, which is galvanically or electromagnetically connected to the RFID chip, generates a response signal directly (i.e., immediately, without waiting for a second signal). By contrast, a passive RFID chip is initially released merely by a trigger signal of the electromagnetic transmission element. The passive RFID chip is only able to draw energy from a (further) signal of the electromagnetic transmission element and to generate a corresponding response signal following a release of this type (unblocking).

Should the implant be a cardiac pacemaker, a pace signal can be used for the energy transmission, as query signal or as a trigger signal for a passive RFID chip. Here, the energy consumption of the RFID chip is preferably designed such that less than 1% of the energy of the pace signal is necessary for the generation of a response signal. In its function as a trigger signal, the pace signal can be examined in terms of its amplitude, its pulse interval and/or its pulse width by the RFID chip, and the RFID chip can be released depending on the determined amplitude value, pulse interval value, or pulse width value. The amplitude value of a pace signal can be determined, by way of example, by means of a capacitance diode which is arranged in the RFID chip and which performs the correct adaptation of the RFID chip transmission circuit to the determined communication frequency only with the presence of a voltage in a predefined value range. In respect of the pulse interval measurement, the generation of a response signal by the RFID chip is authorized (following excitation via the communication antenna and the electromagnetic transmission element) only if the interval between two pulses of a pace signal or a plurality of pace signals lies in a predefined value range. The same is true analogously for the pulse width. Here, it is preferred if two successive pace signals are generated by the implant in such a way that the interval therebetween is shorter than the absolute refractory period of the muscle tissue. These signals have no physiological effect. It is also preferred if, when the cardiac pacemaker is operated with LV Pacing VV Delay Zero, a VV Delay different from zero is used once for a trigger signal.

At least the above object(s) is additionally achieved by a method for identifying an above-described electrode lead by means of an above-described implant, wherein the implant is connected to the electrode lead, said method comprising the following steps:
   generating an electromagnetic query signal by the control unit and forwarding said signal to the communication antenna connected to the control unit;
   transmitting the electromagnetic query signal by the communication antenna, for example a high-frequency signal in a suitable frequency range (for example at 860 MHz);
   receiving the query signal by the transmission element by means of electromagnetic or inductive coupling;
   forwarding the received query signal to the RFID chip;
   processing the received query signal by the RFID chip;
   generating a corresponding electromagnetic response signal by the RFID chip and transmitting the response signal to the transmission element;
   receiving the response signal by the communication antenna of the implant by means of electromagnetic or inductive coupling to the transmission element and forwarding said signal to the control unit; and
   processing the forwarded received response signal in the control unit.

The method according to the present invention is a simple method with which it is possible that information relating to an electrode lead can be identified by means of the implant. As a result of the method according to the present invention, no additional unit is required for querying the electrode leads. The query is performed by the implant itself and enables an assignment of the electrode lead to a channel of the implant. The concept in addition manages with little energy, such that the energy provided by the energy store of the implant can be used for the sensor technology and the therapy. Furthermore, the SAR load (SAR=specific absorption rate) of the patient is minimized.

In one exemplary embodiment of the method according to the present invention, the query signal is generated by the control unit following the occurrence of a predetermined event, preferably following the connection of an electrode lead to the implant, i.e., if a (permanent) galvanic contact is established between the at least one electrical conductor of an electrode lead and an associated contact element or pole arranged on the inner wall of a socket of the implant.

The establishment of a galvanic contact of this type can be detected by means of one of the following methods or a combination of the methods described hereinafter. This identification is performed preferably by means of the above-described detection unit. This detection unit is preferably connected to the control unit or is integrated therein and transmits the result of the detection method to the control unit.

i) The detection unit measures an electrode impedance (at a frequency less than 1 MHz) between two contact elements arranged on a socket. If the electrode impedance lies within a range between 10Ω and 2000Ω the detection unit determines a galvanic contact.

ii) The detection unit measures voltage signals between two contact elements arranged on a socket. If the measured voltage is between 0.5 mV and 200 mV, the detection unit determines a galvanic contact.

iii) The detection unit measures the periodicity of the voltage signals applied by the detection unit between two contact elements arranged on a socket. If the periodicity lies within a value range between 20 bpm and 200 bpm, the detection unit determines a galvanic contact.

iv) The detection unit measures the resonance frequency of the communication antenna continuously or at predefined, fixed intervals. If the detection unit determines a shift (detuning) of the resonance frequency of the antenna by more than 50% of the value otherwise measured, a galvanic contact has been established.

The values specified in the above possibilities for determining galvanic contact between the electrical conductor of an electrode lead and a contact element or pole of a socket of the implant are to be understood as exemplary. The value ranges for identifying the contact can be determined beforehand individually for the implant in question or the implant type in question and/or can be programmed in from outside (input again or changed).

In a further exemplary embodiment of the method according to the present invention, it is provided that, if two or more than two electrode leads are connected to the implant, wherein one of these electrode leads was connected last to the implant, the above-described identification method is carried out for all connected electrode leads in succession, and that each response signal is compared with the information relating to the electrode leads already stored in a memory unit of the implant and the information relating to the electrode lead connected last is assigned to the corresponding socket of the implant on the basis of the result of the comparison. By means of an internal logic, the channels of the implant can additionally be assigned to the plugged-in electrode leads. This can be implemented, for example, in that a comparison of the result of the reading process triggered last with previous reading processes allows the identification of an electrode lead connected last. Together with information stored in a memory of the implant relating to which channel was last connected, a linking of the electrode information to the channel is possible.

In a further exemplary embodiment of the method according to the present invention, the querying of the electrode lead is carried out by generating the electromagnetic query signal in a limited time window following the predetermined event, for example, over a time period of 1 second, so as not to unnecessarily load the energy reserves of the implant by the electrode lead query. Alternatively or additionally, the query of the electrode lead can be controlled depending on the signal of a motion sensor arranged in the housing of the implant. If, by way of example, the motion sensor detects a rest phase of the implant in the event of a movement that is smaller than a predefined threshold value, the querying of the electrode lead is interrupted. Here, it is assumed that the plugging of a plug of an electrode lead into the implant is associated with a movement of the implant.

Alternatively or additionally to the above-explained approach, the socket of the implant can be assigned to an electrode lead and associated information thereof by using the reception strength of the response signal received by means of the communication antenna and forwarded to the control unit.

In a further exemplary embodiment the method according to the present invention and the implant according to the present invention can be used to identify a blind plug. A blind plug can be used if not all sockets of an implant with a plug for an electrode lead are used. In such a case, an unused socket of the implant is occupied by a blind plug. This serves for the purpose of closing off an unused socket so that no liquid infiltrates the socket. Similarly to an electrode lead, a blind plug can also be provided with an RFID chip according to the above example. A blind plug equipped in this way can then be identified similarly to an electrode lead. Thus, the blind plug can be assigned to a specific socket of the implant and also can be identified as being a blind plug.

By means of the electrode lead according to the present invention, the implant according to the present invention, and the method according to the present invention, information relating to the electrode lead can be read in a simple and economical way. The power requirement for reading the information is significantly reduced by the signal path via a transmission element and a communication antenna. As a result, the SAR load of the patient is also reduced. Furthermore, it is not necessary in the case of the solution according to the present invention to switch off EMI protection capacitors integrated in the implant during such a querying of data of the connected electrode lead.

Further features, aspects, objects, advantages, and possible applications of the present invention will become apparent from a study of the exemplary embodiments and examples described below, in combination with the Figures, and the appended claims.

DESCRIPTION OF THE DRAWINGS

The above and other aspects, features and advantages of at least one embodiment of the present invention will be more apparent from the following more particular description thereof, presented in conjunction with the following drawings, wherein.

DETAILED DESCRIPTION

The following description is of the best mode presently contemplated for carrying out at least one embodiment of the present invention. This description is not to be taken in a limiting sense, but is made merely for the purpose of describing the general principles of the present invention. The scope of the present invention should be determined with reference to the claims.

Figure 1:
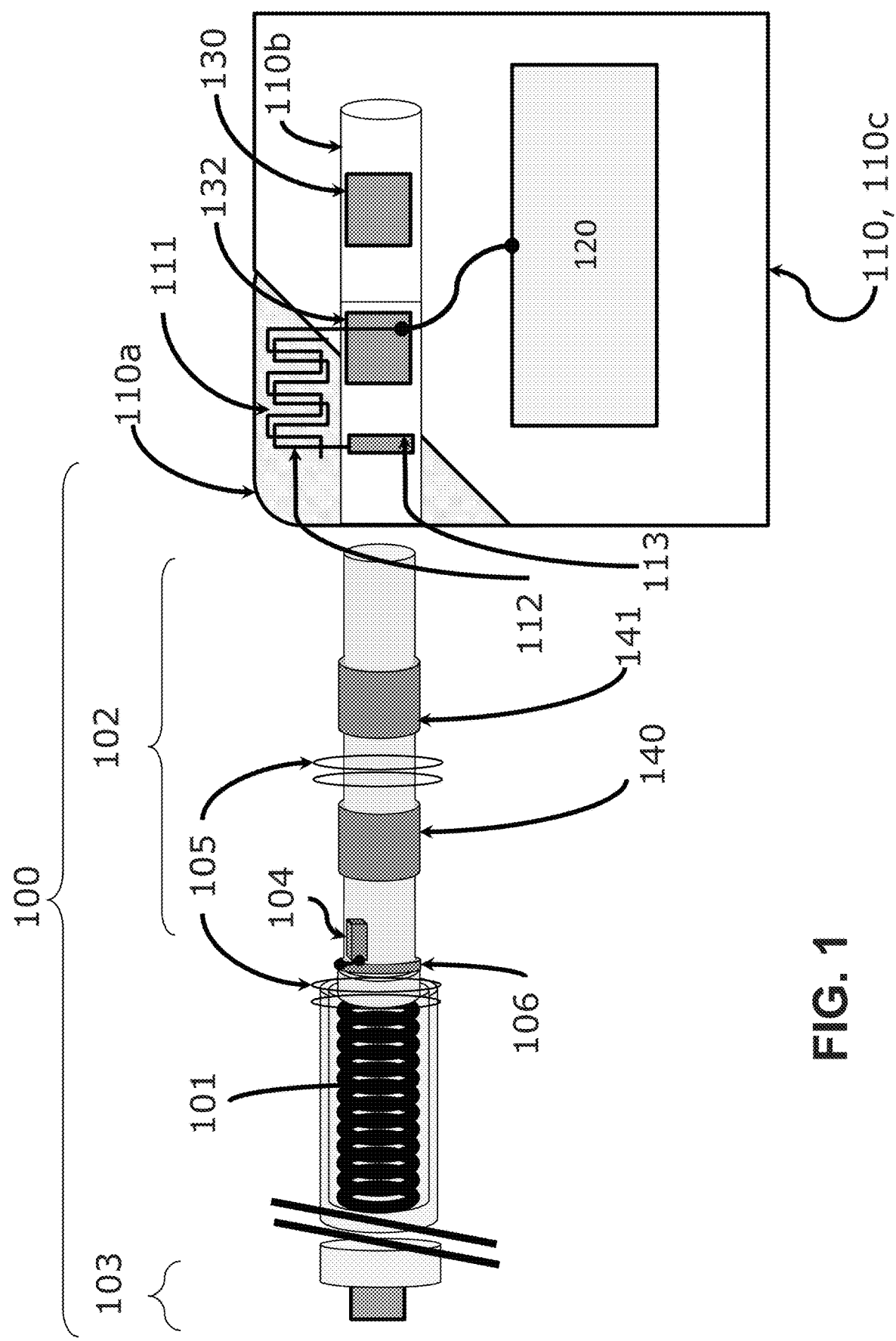
FIG. 1 shows a first exemplary embodiment of an electrode lead according to the present invention and an implant according to the present invention, in a perspective view from the side and in a sectional illustration, respectively.

FIG. 1 shows a first exemplary embodiment of an electrode lead 100 according to the present invention (for example, an electrode lead for bradycardia treatment or tachycardia treatment or neurostimulation) comprising an electrical conductor 101. Alternatively, a plurality of electrical conductors 101 can also be provided. At the distal end 103 of the electrode lead 100, there is arranged an electrode tip, which establishes the electrical contact to the surrounding environment, for example, the patient's tissue. The electrode tip can be formed as a stimulation electrode, measurement electrode, or sensing electrode. A plug 102 is arranged at the proximal end of the electrode lead 100 and can be plugged into a socket 110b of an active implant 110 (likewise shown). The socket 110b protrudes into a header 110a of the implant 110. The implant 110 often has a plurality of sockets 110b, which can each be connected to an electrode lead 100. The active implant 110 can be formed, by way of example, as a cardiac pacemaker or defibrillator. As a result of the plug 102, a mechanical and electrical connection exists between the electrode lead 100 and the active implant 110. An electrically conductive (galvanic) connection exists between the electrical conductor 101 of the electrode lead 100 and the internal electrical components of the implant 110, for example, a control unit 120, via corresponding contact elements 140, 141 (e.g., poles, connection points) of the plug 102 and contact elements 130, 131 (e.g., poles, connection points) of the socket.

An RFID chip 104 is integrated into the plug 102 (for example, IS1 plug, IS4/DF4 plug). This has the advantage that the RFID chip 104, once the plug 102 has been plugged into the socket 110*b* of the implant 110, is arranged within the rigid header 110*a* of the implant 110 in which the socket 110*b* is provided and is therefore protected against high mechanical load (e.g., bending/abrasion). The RFID chip 104 is encased by the insulation of the plug 102 in a hermetically sealed manner apart from a chip contact element 106 electrically conductively connected to the RFID chip. The chip contact element 106, by way of example, consists of a metallization in the form of a ring, preferably containing gold and/or platinum, arranged externally on the plug 102 of the electrode lead 100. The chip contact element 106 is arranged at a distance from the therapeutically used contact elements 140, 141 of the plug 102.

Alternatively, the RFID chip 104 can be arranged between an insulation sheath, embodied, for example, as a silicone sheath, and an insulation sleeve (not illustrated) provided at the proximal end of the electrode lead 100 in the region of the plug 102. The insulation sleeve can be embodied as a separate add-on part, which can be slid over the insulation sheath. By way of example, the add-on part can have a length of 500 μm and a thickness of 100 μm. The insulation sleeve which, for example, consists of a liquid-crystal polymer (LCP), silicone, a ceramic and/or glass, surrounds the installation sheath in such a way that the RFID chip 104 is hermetically sealed with respect to the surrounding environment.

For example, a chip for the frequency range between 840 MHz and 960 MHz can be used as RFID chip 104. Furthermore, a memory capacity of 512 bits, freely writable, and 240 bits for storage of the electronic product code (EPC) can be provided. The memory of the RFID chip 104 can be read and/or written both at the time of manufacture in the factory and during the execution of the method according to the present invention for identifying an electrode lead. Information for identifying the electrode lead 100 and for use thereof can be contained in the memory of the RFID chip 104. Such information can include: the manufacturer, the type of electrode lead, the serial number, the date of manufacture, regions of approval, approval conditions, implantation date, implantation compatibilities, MIll compatibility, and the like. The memory of the RFID chip 104 can also contain security mechanisms and security information, which ensure or display the integrity (for example, in the case of partial data loss) and the authenticity (for example, in the case of manipulation) of the stored information.

As already mentioned above, the implant 110 contains a control unit 120 in an outwardly hermetically sealed housing 110*c*, which control unit is connected to the contact element 132 or the contact elements 130, 132 for the electrode lead 100. Once an electrode lead 100 has been plugged into a corresponding socket 110*b* in the header region 110*a* of the implant 110, an electrically conductive (galvanic) connection exists between the control unit 120 and the one electrical conductor 101 or the plurality of electrical conductors 101 of the electrode lead 100. This is achieved by feed-throughs inside the encapsulated implant 110.

A communication antenna 111 is also provided in the header 110*a* of the implant 110 and is matched to the communication frequency. The communication antenna 111 can also be used as an antenna for data transmission to an external receiver for the contacting of a data and service center. The communication antenna 111 is electrically conductively connected to the control unit 120 via a feed-through. In a preferred embodiment, the circuit of the communication antenna 111 is designed such that it has at least two resonances, such that two separate channels are available for the communication with the electrode leads 100 and for the communication for other purposes, such as communication with an external unit for contacting a data and service center or for radio telemetry, in particular also simultaneously.

In addition, in the exemplary embodiment illustrated in FIG. 1, an electromagnetic transmission element in the form of a second antenna 112 is provided in the header 110*a*. The antenna 112 is arranged in such a way that, with the used UHF, it couples RFID frequency electromagnetically or inductively as optimally as possible with the communication antenna 11. The antenna 112 is galvanically connected to a contact element (e.g., pole, connection point) 113 which is arranged on the inner surface of the socket 110*b* and which is arranged at a distance from the therapeutic contact elements 130, 132.

Once the plug 102 has been correctly plugged into the socket 110*b*, the chip contact element 106 connected to the RFID chip 104 is galvanically connected to the contact element 113 of the socket 110*b*. This results in a galvanic connection between RFID chip 104 and the antenna 112.

Figure 2:
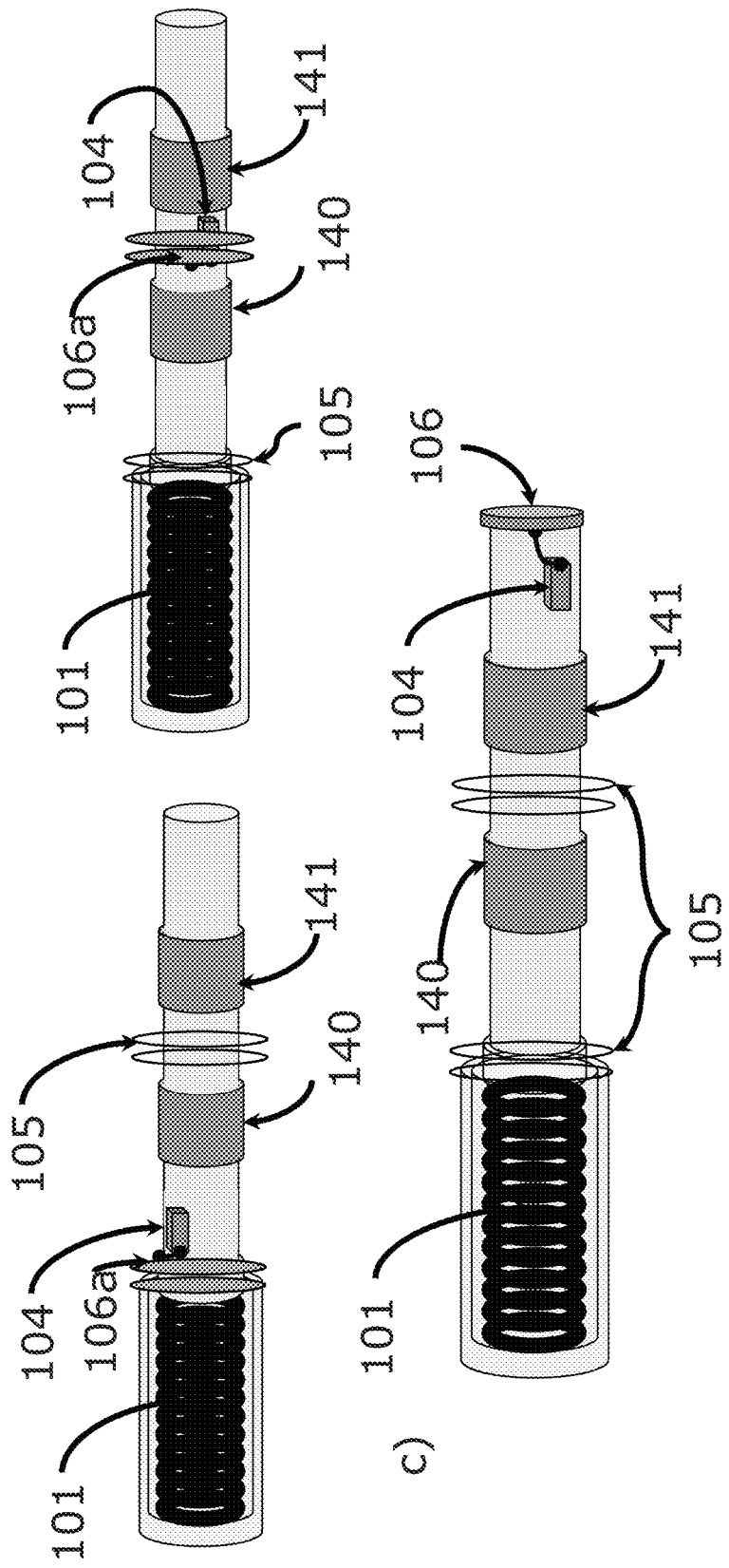
FIGS. 2A-C shows a second to a fourth exemplary embodiment of an electrode lead according to the present invention, in each case in a perspective view from the side.

The contact between the RFID chip 104 and the antenna 112 arranged in the header 110*a* can also be established in a different way when the plug 102 is plugged into the socket 110*b*. An alternative possibility is illustrated by way of example on the basis of FIG. 2C. The annular chip contact element 106, which is connected to the RFID chip 104, is arranged in this exemplary embodiment at the proximal end of the plug 102. Alternatively, the contacting can be produced via metallized sealing lips 106*a*, which are also galvanically connected to the RFID chip 104, as illustrated in FIGS. 2A and 2B. In addition, further sealing lips 105 can be provided in order to seal the plug connection.

The active implant 110 also has a filter unit (not illustrated) for filtering electromagnetic interference (EMI filter), for example, so as to prevent the infiltration of mobile telephone signals into the encapsulated housing of the implant 110. The filter unit short-circuits high-frequency signals (frequency>1 kHz) to electrical ground. For example, capacitors connected in parallel and having a high capacitance are used for this purpose.

The method according to the present invention for identifying an electrode lead by means of the implant 110 shown in FIG. 1 will be explained hereinafter.

When the control unit 120 of the implant detects, by means of a method described below, whether an electrode lead 100 has been connected beforehand to a socket 110*b* of the implant 110, the identification method according to the invention for the electrode lead is started. The control unit 120 generates an electromagnetic query signal, which is forwarded to the communication antenna 111 and is transmitted thereby. A query signal of this type can be, for example, a high-frequency signal in a suitable frequency range (for example, 860 MHz). The query signal is coupled into the antenna 112 by the local vicinity and is forwarded by the antenna via the galvanic connection to the RFID chip 104 of the plugged-in electrode lead 100. The RFID chip 104 is activated by the query signal and processes the query signal. The response signal generated on account of this activation by the RFID chip 104 and containing, for example, the above-specified information regarding the electrode lead 100 taken from the memory of the RFID chip 104 is transmitted by the RFID chip 104 to the antenna 112 in the header 110*a* of the implant 110 and is transmitted thereby. By means of the electromagnetic coupling between antenna 112 and communication antenna 111 in the header 110*a*, the communication antenna 111 receives the response signal sent out by the antenna 112 and transmits this to the control unit 120. The control unit 120 evaluates the transmitted response signal and assigns the information obtained from the electrode lead 100 for identification of the electrode lead 100 to the corresponding socket 110*b* or the channel.

Due to the spatially close arrangement between the hermetically encapsulated RFID chip 104, antenna 112, and communication antenna 111, a sufficiently good coupling can be established, even with poor galvanic contacting of the contact elements constituted by the plug 102 and socket 110*b*. Typically, the shortest distance between the antenna 112 and the communication antenna 111 is less than 12 mm.

Figure 3:
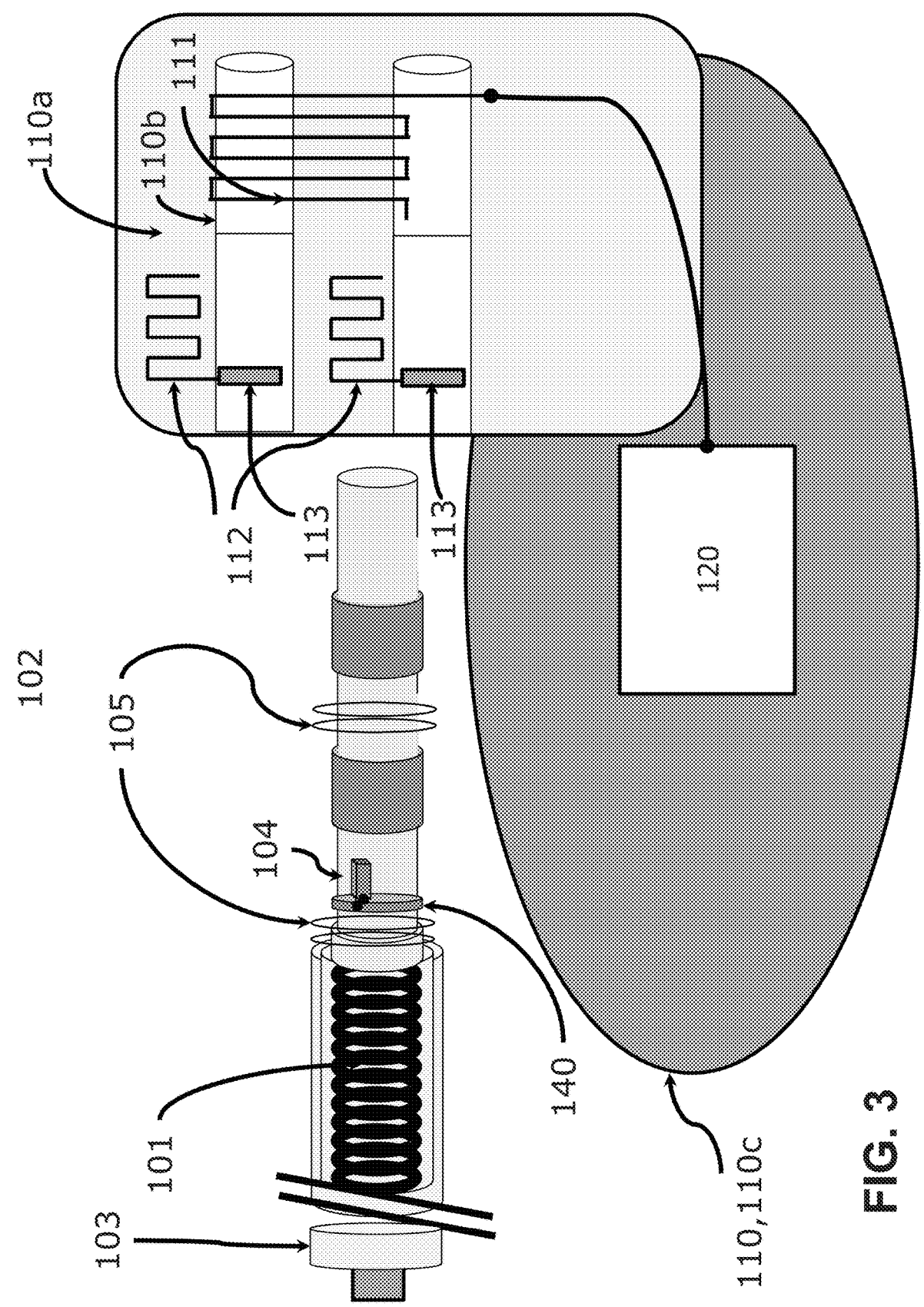
FIG. 3 shows a fifth exemplary embodiment of an electrode lead according to the present invention and a second exemplary embodiment of an implant according to the present invention in a perspective view from the side and in a sectional illustration, respectively.

If a plurality of sockets 110*b* are arranged in the header 110*a* of the implant (see FIG. 3), there is an assignment of the individual electrode leads 100 to the sockets 110*b* of the implant 110 or to the corresponding channel via a logic within the implant 110. The newly connected electrode lead 100 is identified with the aid of a comparison with the last-triggered identification process and a querying of all plugged-in electrode leads in succession. For a querying of this type, the header 110*a* of the implant 110 illustrated in FIG. 3 has a separate antenna 112 for each socket 110*b* in order to enable the spatial assignment of the transmitted signals to a specific socket. By contrast, merely a single communication antenna 111 is provided, which, as shown in FIG. 3, extends over the header 110*a* in such a way that it is electromagnetically or inductively coupled to both antennas 112. The control unit 120 of the implant compares the information stored in a memory relating to the electrode leads 100 from previous query methods with the received response signals of the electrode leads 100 and, on the basis of this comparison, assigns the information relating to the newly connected electrode lead 100 to the corresponding contact elements of the implant 110 of the corresponding socket 110*b*. With regard to the assignment to the channel of the implant 100 with which the electrode lead in question has been contacted, it is necessary that the control unit 120 of the implant 110 independently detects whether an electrode lead is connected to a channel, and, if so, which channel. On the basis of the information relating to the newly connected electrode lead and also on the basis of the knowledge of which channel was last connected, a linking between the information relating to the electrode lead and the connected channel is possible.

In order to ensure that the electrode lead 100 is detected in a sufficient time resolution, without unnecessarily loading the energy reserves of the implant 112 by a querying of excessively high frequency, the implantation process associated with a plugging-in of the electrode leads can be detected via a position sensor arranged in the implant 110 and/or a motion sensor in the implant 110. Accordingly, a query signal is generated by means of the control unit 120 only if the position sensor and/or the motion sensor determines/determines that an implantation has been performed. If, on account of the presence of a plurality of sockets 110*b*, a plurality of query signals are generated, the time interval of the querying is thus preferably less than 1 second.

Following a successful identification of the electrode lead or the electrode leads, the high-frequency querying of the channels in question is switched off. In a further exemplary embodiment, a predefinable rest phase can be temporally determined following a concluded querying, during which rest phase the movement is below a predefined threshold value. The start of the rest phase also ends a querying of the unoccupied sockets.

Figure 4:
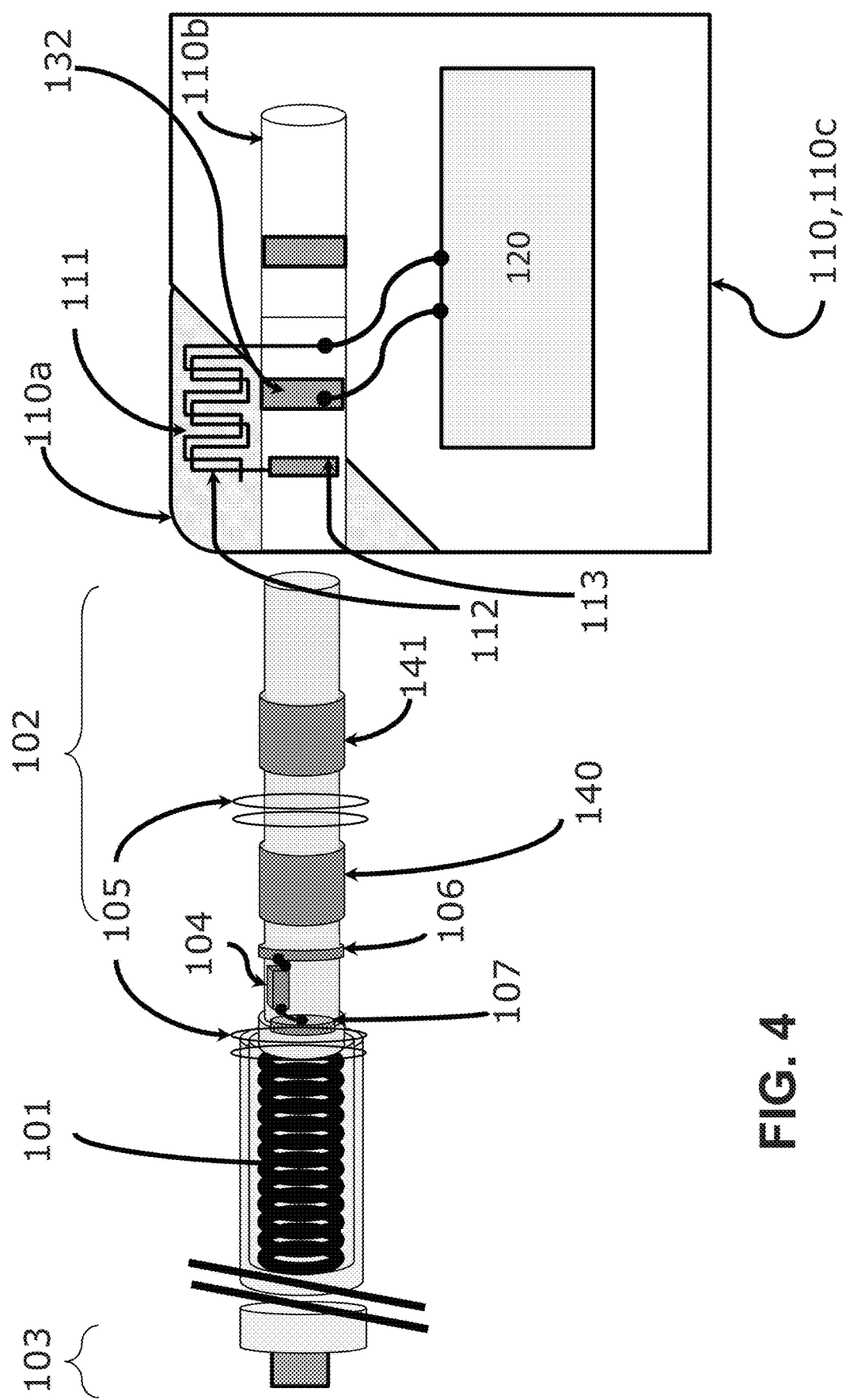
FIG. 4 shows a sixth exemplary embodiment of an electrode lead according to the present invention and a third exemplary embodiment of an implant according to the present invention in a perspective view from the side and in a sectional illustration, respectively.

In a further exemplary embodiment, which is shown in FIG. 4, the RFID chip, in addition to the galvanic connection to the contact element 106, is also galvanically contacted with a larger metallic element (for example, in the form of a metal ring) 107, which is capacitively coupled to the electrical conductor 101 of the electrode lead and thus serves as a ground plane of the RFID chip 104. In this exemplary embodiment, a therapeutically used contact element 132 of the socket 110*b* is connected to the ground of the implant 110. As the plug 102 of the electrode lead 100 is plugged into the socket 110*b*, a therapeutic contact element 140 of the electrode lead 100 is connected to the contact element 132 on the socket 110*b*, such that the connection of the RFID chip 104 to the ground of the implant 110 is established via the capacitive coupling to the electrical conductor 101 connected to the contact element 140.

Figure 5:
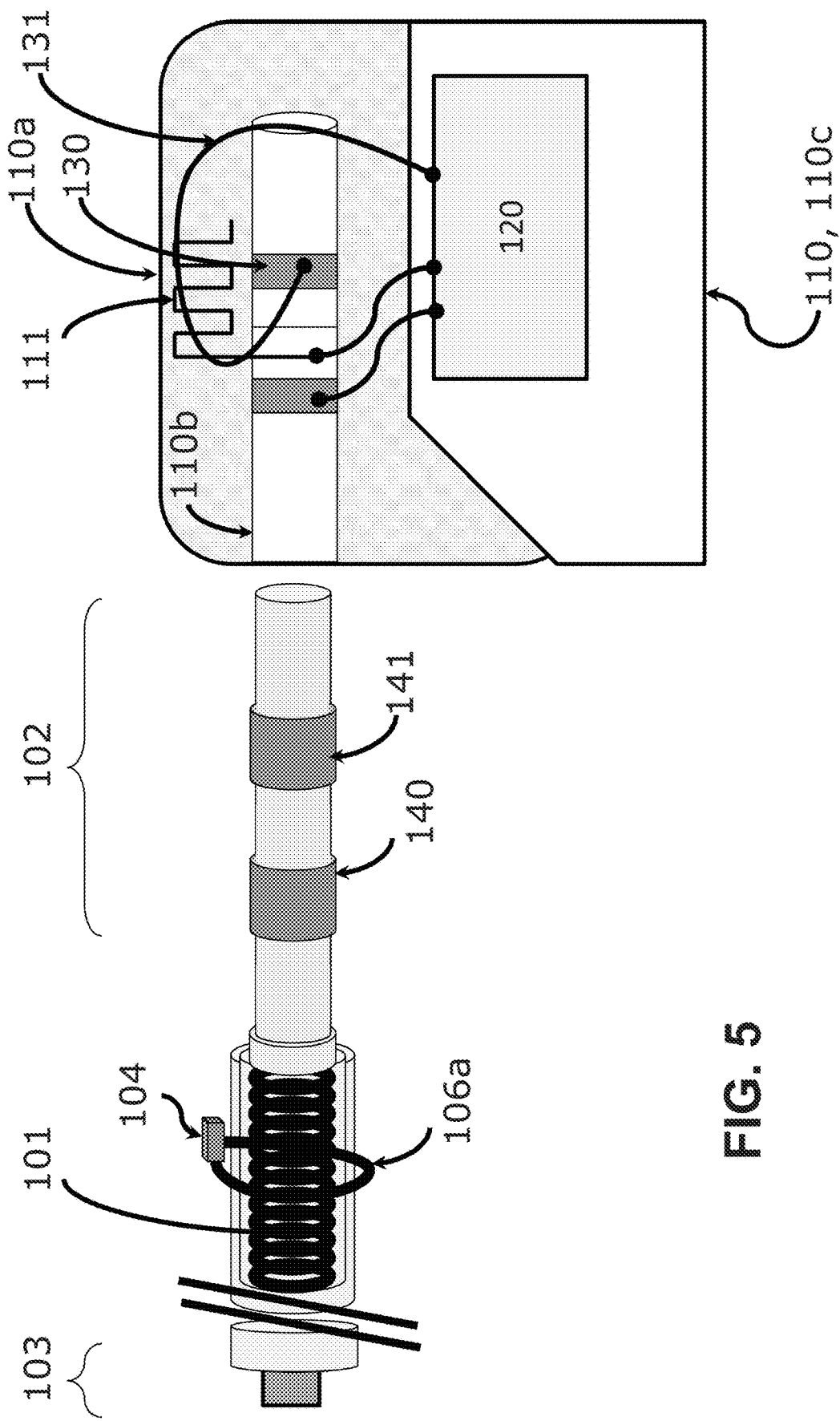
FIG. 5 shows a seventh exemplary embodiment of an electrode lead according to the present invention and a fourth exemplary embodiment of an implant according to the present invention in a perspective view from the side and in a sectional illustration, respectively.

In the exemplary embodiment shown in FIG. 5, a further alternative for the coupling of the RFID chip 104 to an electrical conductor 101 of the electrode lead 100 is illustrated. The RFID chip 104 is connected to a conductor loop 106*b*, which is coupled contactlessly to the electrical conductor 101. Instead of the second antenna 112, an electrical conductor component 131 (e.g., conductor loop) is also provided in the header 110*a* as electromagnetic transmission element which is electromagnetically or capacitive coupled to the communication antenna 111. The electrical conductor component 131 is connected at one end to the control unit 120 and at its other end to a contact element 130, preferably also used therapeutically, of the socket 110*b*. As the plug 102 is plugged into the socket 110*b*, a galvanic connection is established to a corresponding contact element 140 of the plug 102 and thus to the electrical conductor 101 of the electrode lead 100.

The electrical conductor component 131 runs close, preferably parallel to the communication antenna 111, such that, with the used UHF, it couples RFID frequency electromagnetically or inductively to the communication antenna 111 as optimally as possible. The conductor component 131 particularly preferably runs over a length of at least 5 mm parallel to the communication antenna 111. Here, the distance of the communication antenna 111 from the conductor component 131 is preferably less than 12 mm. If the communication antenna 111 is formed as a loop antenna, it is preferable that the areas spanned by the communication antenna 111 and the conductor component 131 largely overlap with one another. In other words, the magnetic flux of the communication antenna 111 and the magnetic flux of the conductor component 131 should flow through one another to the best possible extent. The magnetic coupling factor between the communication antenna 111 and the conductor component 131 is preferably at least 0.1.

In one exemplary embodiment, the conductor component 131 is connected via a capacitor (not illustrated) to the electrically conductive housing 110*c* close to the entry point into the electrically conductive housing 110*c* of the implant 110 (for example, closer than 20 mm), wherein the capacitor can be used as EMI protection. Possibilities for the dimensioning of the capacitor have already been explained above.

In this exemplary embodiment as well, electrode leads 100, which are disposed in the immediate vicinity of the header 110a, but which are not contacted with the active implant, are not read. This increases the reliability of the electrode lead identification.

In the querying direction, the path of the query signal thus runs from the control unit 120 via the communication antenna 111, the electrical conductor component 131, the electrical conductor 101 of the electrode lead 100, and the conductor loop 106b to the RFID chip 104. The signal path of the response signal runs in the opposite direction.

Figure 6:
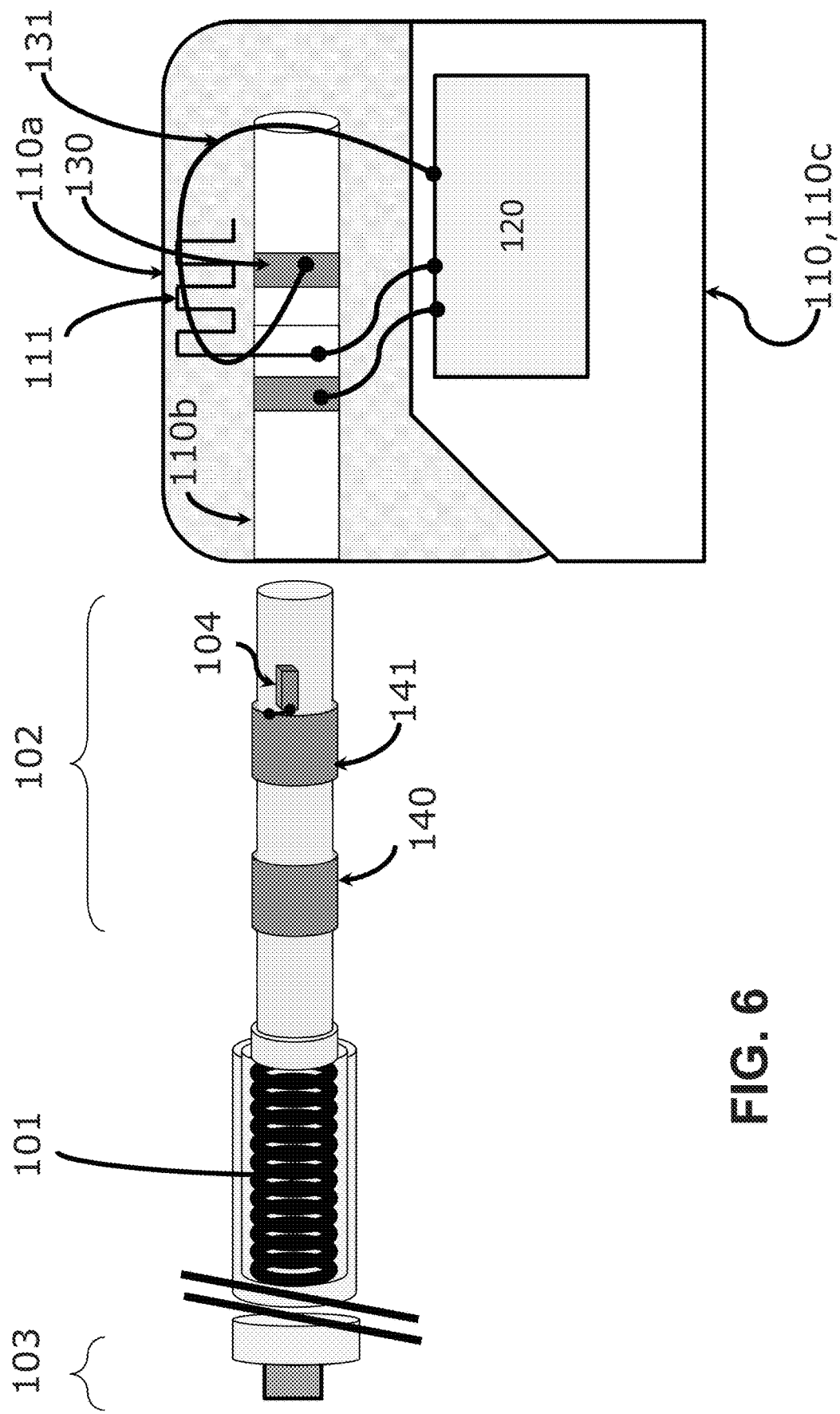
FIG. 6 shows an eighth exemplary embodiment of an electrode lead according to the present invention and a fifth exemplary embodiment of an implant according to the, present invention in a perspective view from the side and in a sectional illustration, respectively.

In the exemplary embodiment illustrated in FIG. 6, a direct galvanic coupling is provided between the RFID chip 104 and a therapeutically used contact element 141 of the plug 102 of the electrode lead 100. With regard to the implant, the structure is similar to FIG. 5. The RFID chip 104 is preferably connected to the contact element 141, which has a coating with the highest inductance and/or resistance value of the electrode lead 100 in question. The influence of the electrical conductor 101 arranged distally as considered from the contact element 141 on the transmission properties of the RFID chip is thus minimized.

Figure 7:
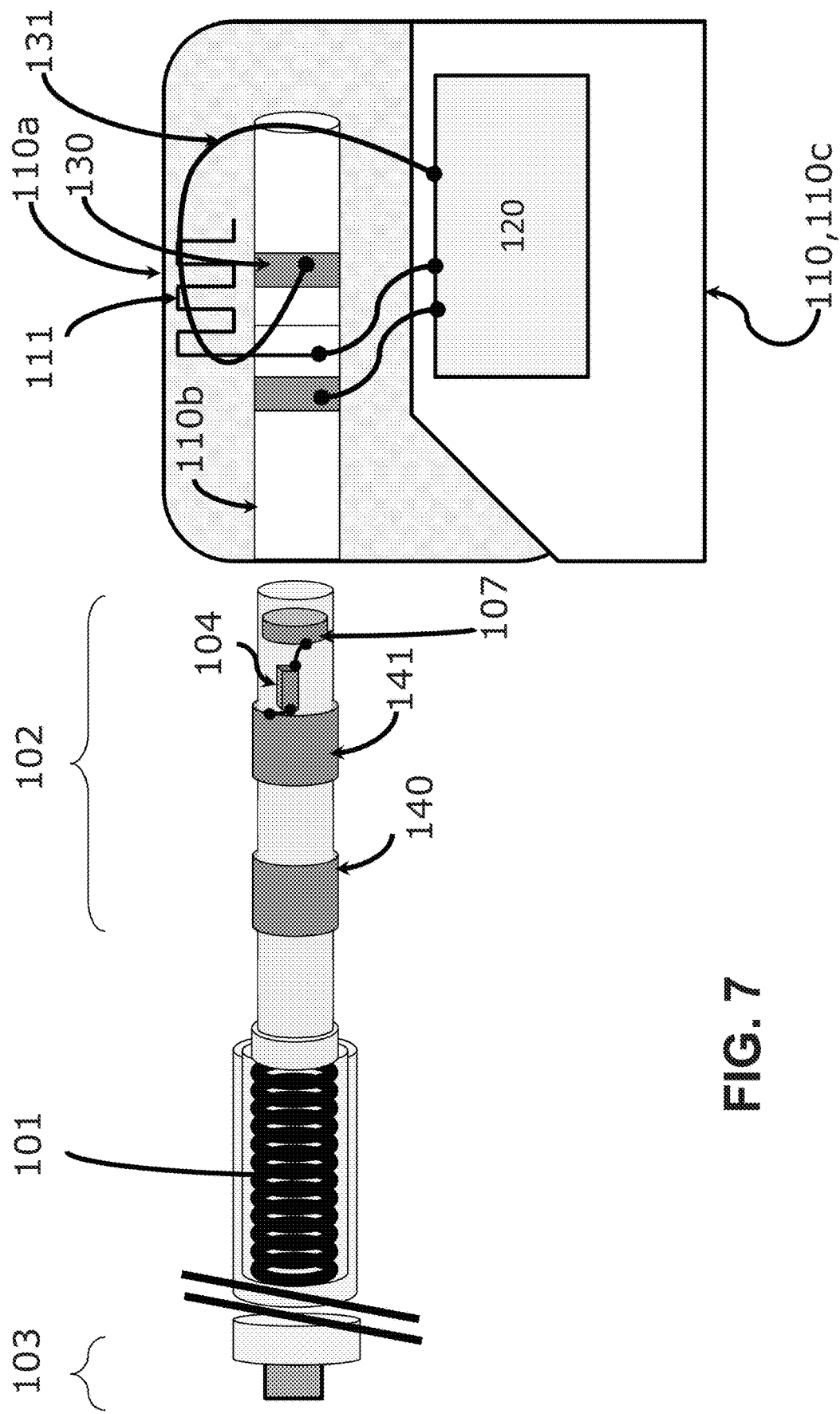
FIG. 7 shows a ninth exemplary embodiment of an electrode lead according to the present invention and a sixth exemplary embodiment of an implant according to the, present invention in a perspective view from the side and in a sectional illustration, respectively.

In the exemplary embodiment shown in FIG. 7, the second connection point of the RFID chip 104 is connected to a larger metallic element 107 (for example, in the form of a metal ring). Similarly to the exemplary embodiment explained above on the basis of FIG. 4, a ground plane is hereby provided for the RFID chip 104.

Figure 8:
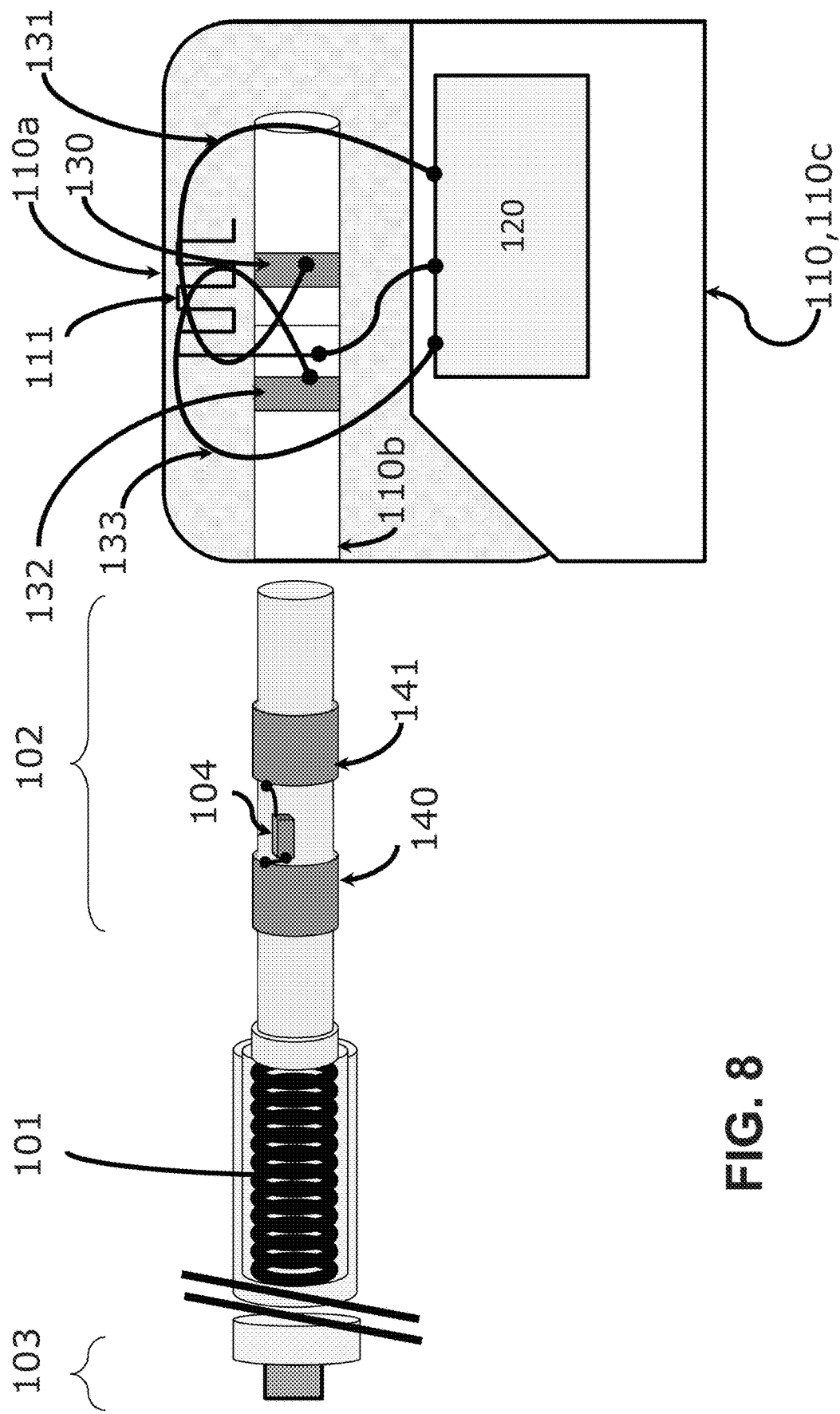
FIG. 8 shows a tenth exemplary embodiment of an electrode lead according to the present invention and a seventh exemplary embodiment of an implant according to the, present invention in a perspective view from the side and in a sectional illustration, respectively.

The exemplary embodiment illustrated in FIG. 8 comprises an RFID chip 104, which is galvanically connected to two therapeutically used contact elements 140, 141. This exemplary embodiment uses two conductor components 131, 133 each as electromagnetic transmission element coupled to the communication antenna 111. In this embodiment, the RFID chip 104 is connected at both ends to the conductor components 131, 133. This results in an improvement of the coupling compared to the situation in which one end of the RFID chip is connected to a larger contact element 107, which serves as a ground plane of the RFID chip 104, since possible interferences on account of fluctuations of the ground plane potential are eliminated as a result.

In a particularly preferred embodiment, the control unit 120 in the RFID chip 104 transmits energy for a short time (preferably for a time shorter than 2 ms) through a galvanic coupling and thus prompts the RFID chip 104 to transmit its electrode lead information. This information is received via the communication antenna 111 and is forwarded to the control unit 120. The control unit 120 knows the time when energy was delivered to which RFID chip 104 and opens a receiving window at an appropriate time, accordingly. An assignment of the corresponding electrode lead 100 to the corresponding socket 110b or the corresponding channel can thus be implemented.

The energy pulse, if the implant is embodied as a cardiac pacemaker, is preferably delivered via a pace or derived therefrom. Here, the RFID chip is designed such that the energy consumption thereof is less than 1% of the pace energy. The internal resistance of the RFID chip 104 is such that, when measured between the contact elements 140, 141 of the plug 102, it is at least 1 kΩ. The internal resistance is particularly preferably greater than 1 MΩ.

Figure 9:
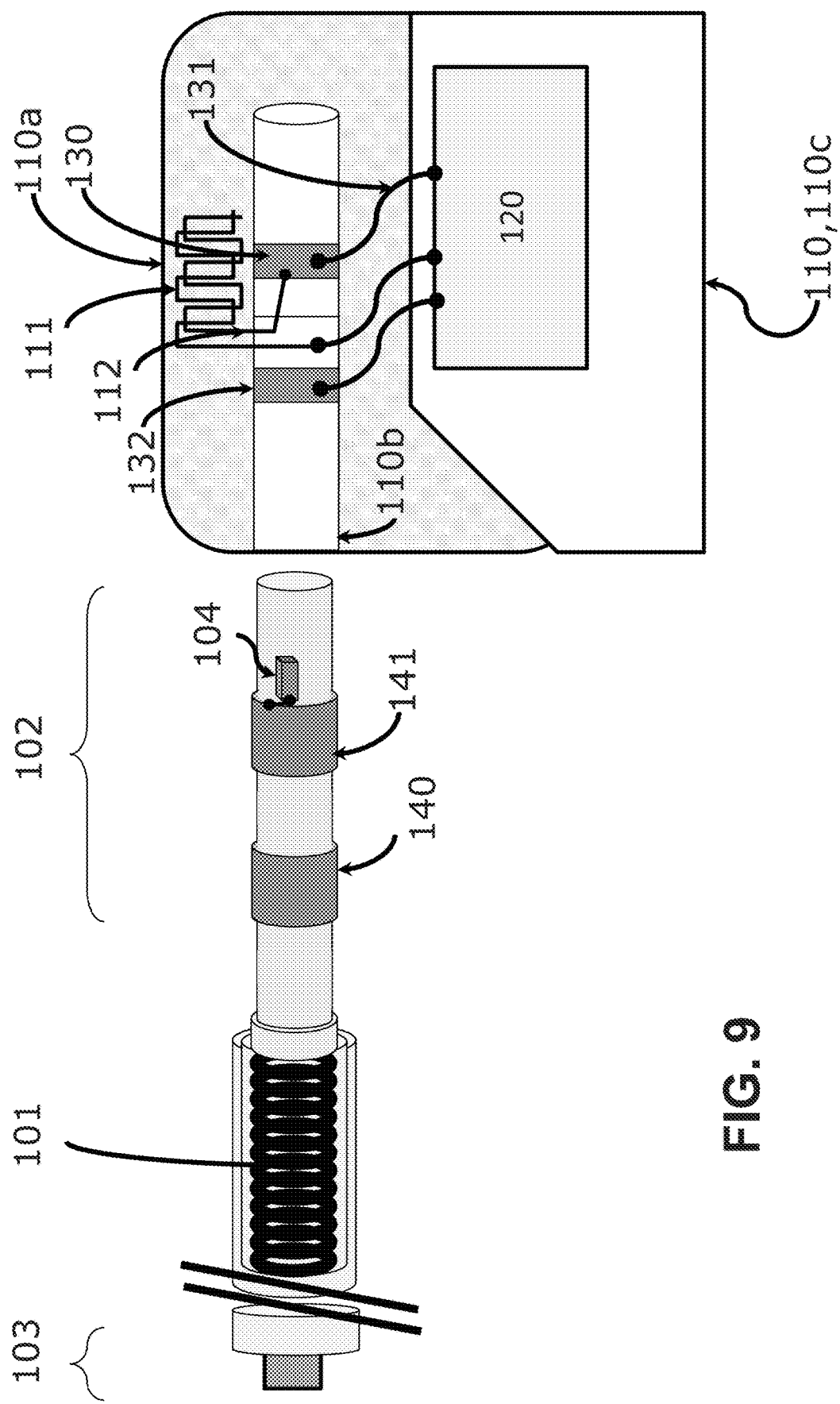
FIG. 9 shows an eleventh exemplary embodiment of an electrode lead according to the present invention and an eighth exemplary embodiment of an implant according to the, present invention in a perspective view from the side and in a sectional illustration, respectively.

The exemplary embodiment illustrated in FIG. 9 is similar to the exemplary embodiment according to FIG. 1, wherein in the variant illustrated in FIG. 9 the RFID chip is directly galvanically connected to a therapeutic contact element 141 of the plug 102 of the electrode lead 100. Accordingly, the antenna 112 is connected to a therapeutically used contact element 130 of the socket 110b.

Figure 10:
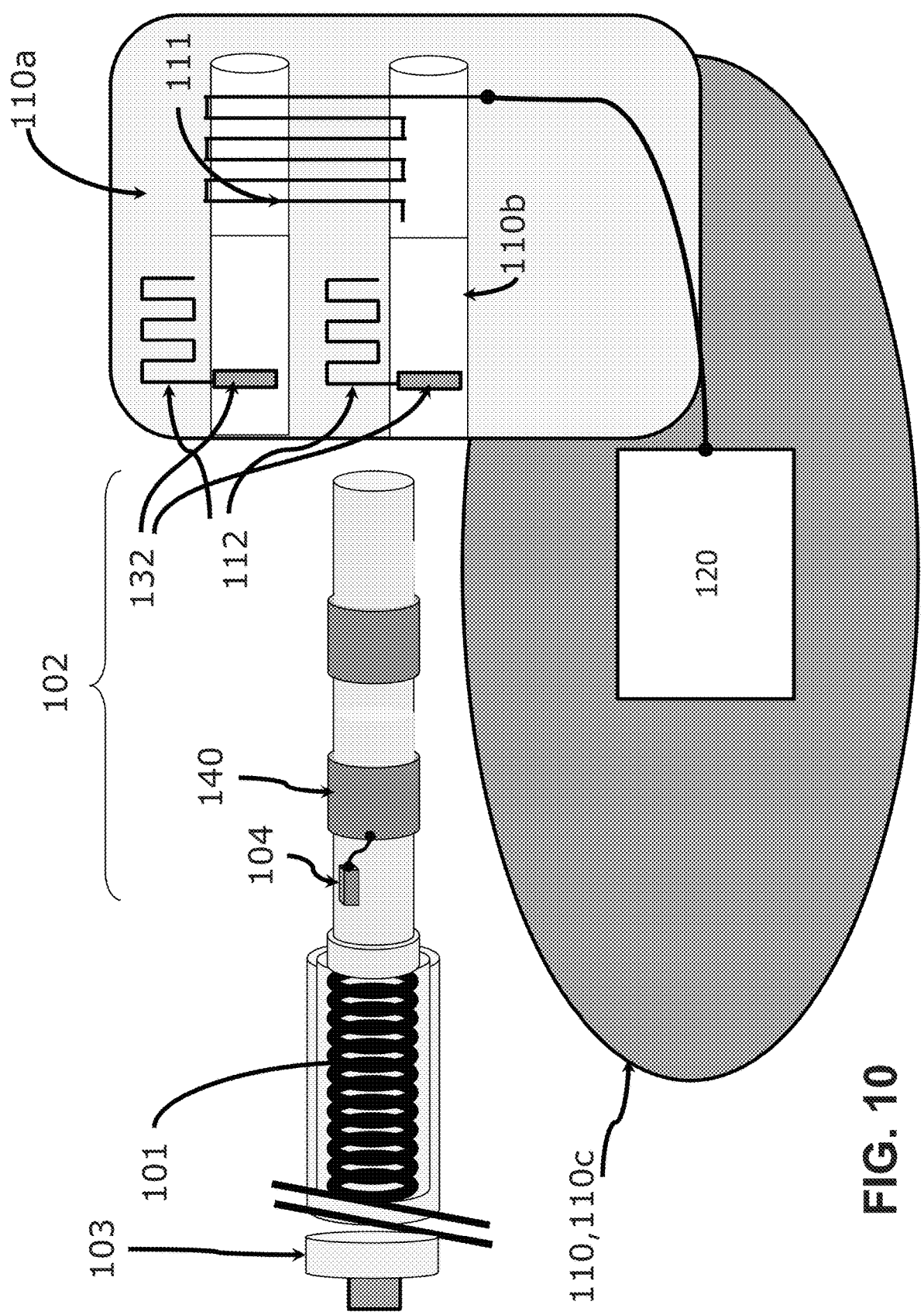
FIG. 10 shows a twelfth exemplary embodiment of an electrode lead according to the present invention and a ninth exemplary embodiment of an implant according to the, present invention in a perspective view from the side and in a sectional illustration, respectively.

The exemplary embodiment illustrated in FIG. 10 relates, similarly to FIG. 3, to a design in which each socket 110b is assigned an antenna 112, whereas the sole communication antenna 111 is designed such that its covers both sockets 110b. The exemplary embodiment according to FIG. 10 differs from the exemplary embodiment according to FIG. 3 in that the RFID chip 104 is directly galvanically connected to a therapeutic contact element 140 of the plug 102 of the electrode lead 100. Accordingly, the second antenna 112 assigned to each socket is galvanically connected to a therapeutically used contact element 132 of the socket 110b.

As already explained above, the RFID chip 104 can be active or passive. In the case of a passive design of the RFID chip 104, above-presented methods for activating the RFID chip 104 can be used.

In a preferred exemplary embodiment, the implant has a detection unit (not illustrated), which detects the contacting of an electrode lead 100 with the implant 110 or the correct plugging of a plug 102 of an electrode lead 100 into a socket 110b. The methods by means of which a detection unit of this type, which is connected to the control unit 120, can determine that the plug 102 has been contacted or correctly plugged in have already been explained above. A detection unit of this type, in accordance with the present invention, can be used in all above-explained exemplary embodiments of the implants.

As a result of the present invention, electrode-specific information of all electrode leads 100 coupled to an implant 110 are read, without posing any risk to the therapeutic path due to a serial galvanic coupling or additional electrical components. The RFID chip 104 is only contacted with a communication antenna 111 by the contacting with the implant 110. The electrode lead 100 is assigned to the corresponding socket 110b or channel via the targeted addressing of the sockets/channels by the active implant 110. The power requirement for identification is significantly reduced compared to a reading of an RFID inlay (with antenna) via a transmitting antenna at the active implant. In addition, no measures are necessary for bypassing the function of the EMI filter for the reading operation. It is also advantageous that the RFID chip is small and, for example, has a much smaller spatial requirement than an RFID inlay (with antenna). The arrangement of the transmission element in the header 110a means that the transmission element is exposed only to small mechanical loads.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SIGNS 100 electrode lead
101 electrical conductor
102 plug
103 distal end of the electrode lead
104 RFID chip
105 sealing lips 106 chip contact element
106a metallized sealing lips
106b conductor loop
107 metallic element
110 implant
110a header of the implant
110b socket
110c housing
111 communication antenna
112 second antenna
113 contact element
120 control unit
130, 132 contact element of the socket 110b
131, 133 conductor component
140, 141 contact element of the plug 102 of the electrode lead 100

We claim:

1. An implant comprising:
a hermetically tightly sealed housing;
a control unit arranged in the housing;
a header secured to the housing;
at least one socket formed in the header, the at least one socket configured to receive and connect to a plug of an electrode lead;
a communication antenna provided in the header, the communication antenna electrically connected to the control unit; and
at least one electromagnetic transmission element provided in the header in a region of the at least one socket, the at least one electromagnetic transmission element electrically connected to a contact element which is provided on an inner wall of the at least one socket,
wherein the at least one electromagnetic transmission element is electromagnetically or inductively coupled to the communication antenna, and
wherein the at least one electromagnetic transmission element is galvanically connected to the contact element provided on the inner all of the at least one socket.

2. The implant according to claim 1, wherein the at least one electromagnetic transmission element is formed as art antenna or electrical conductor component.

3. The implant according to claim 2, wherein the at least one electromagnetic transmission element comprises an electrical conductor component, and wherein the electrical conductor component is connected to the housing of the implant, the housing being electrically conductive, via a capacitor.

4. The implant according to claim 1, wherein the implant has multiple sockets in the header and a number of electromagnetic transmission elements corresponds to a number of sockets, wherein the communication antenna comprises a sole communication antenna which is electromagnetically or inductively coupled to all electromagnetic transmission elements arranged in and/or on the header.

5. The implant according to claim 1, wherein the control unit is designed in such a way that it generates a separate query signal following an occurrence of a predetermined event for each socket connected to an electrode lead.

6. The implant according to claim 1, Wherein the implant comprises a detection unit which detects a connection of the electrode lead to the implant.

* * * * *